United States Patent [19]

Ulbrich

[11] Patent Number: 4,951,815
[45] Date of Patent: Aug. 28, 1990

[54] MEDICAL GLOVE AND LUBRICANT DISPENSING PACKAGE

[76] Inventor: Paul Ulbrich, 75 Rainbow Bridge Pl., San Ramon, Calif. 94583

[21] Appl. No.: 440,698

[22] Filed: Nov. 24, 1989

[51] Int. Cl.⁵ .............................................. B65D 85/18
[52] U.S. Cl. .................................... 206/213; 206/278; 206/438; 206/439
[58] Field of Search ............... 206/213, 278, 438, 439, 206/363

[56] References Cited

U.S. PATENT DOCUMENTS

| 1,053,492 | 2/1913 | Hadfield | 206/278 |
| 3,494,726 | 2/1970 | Barasch | 206/213 X |
| 3,717,533 | 2/1973 | Mayworm et al. | 206/439 |
| 3,942,634 | 3/1976 | Gandi et al. | 206/438 |
| 4,068,757 | 1/1978 | Casey | 206/363 |
| 4,482,053 | 11/1984 | Alpern et al. | 206/439 |
| 4,714,595 | 12/1987 | Anthony et al. | 206/439 X |
| 4,811,847 | 3/1989 | Reif et al. | 206/213 X |

FOREIGN PATENT DOCUMENTS

| 692913 | 8/1964 | Canada | 206/278 |
| 1459068 | 10/1966 | France | 206/438 |

Primary Examiner—William I. Price
Attorney, Agent, or Firm—Harris Zimmerman

[57] ABSTRACT

A sealed package contains a glove of the type worn by medical practitioners when one or more fingers must be inserted into openings in a patient's body and also contains a supply of lubricant for the glove in a separate sealed compartment. The package is formed by sheets of material bonded along zones that define two compartments, the bonding being weaker than the material itself enabling one sheet to be peeled away from the other to open both compartments with one motion of the hands. The package further contains a glove holder which spreads the cuff of the glove to facilitate entry of a hand and which also protects the outer surface of the glove from contamination during the process of putting the glove on.

14 Claims, 2 Drawing Sheets

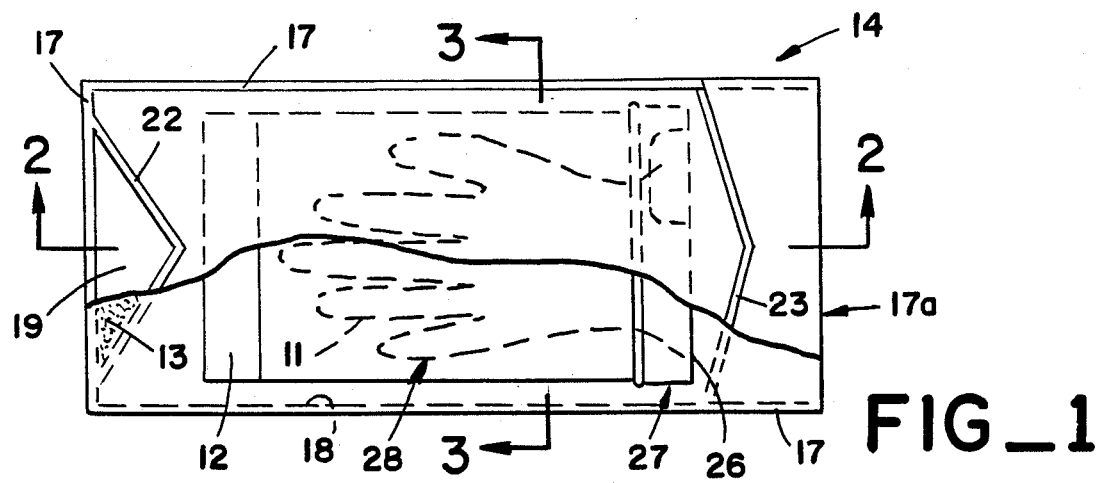
FIG_1
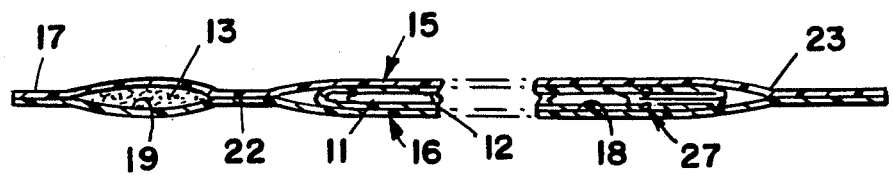
FIG_2
FIG_3
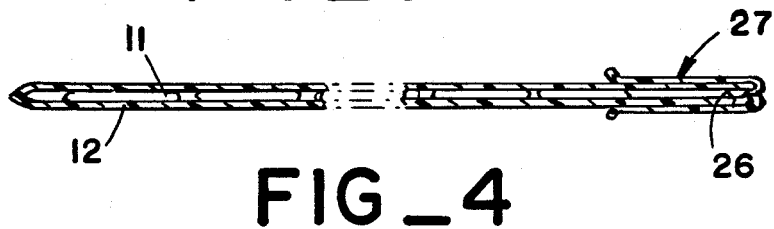
FIG_4
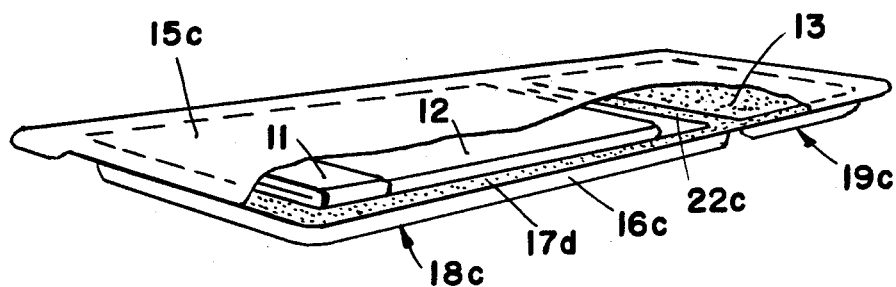
FIG_10

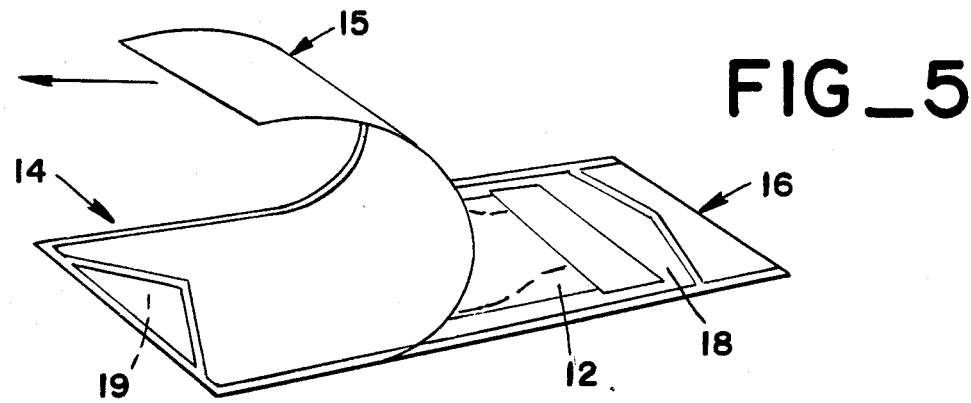
FIG_5
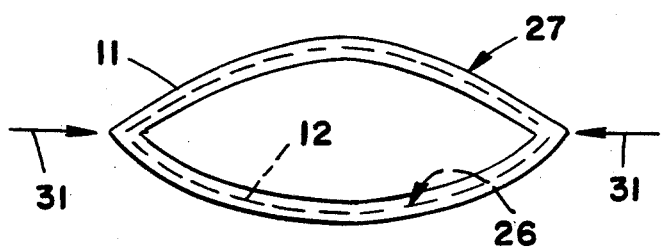
FIG_6
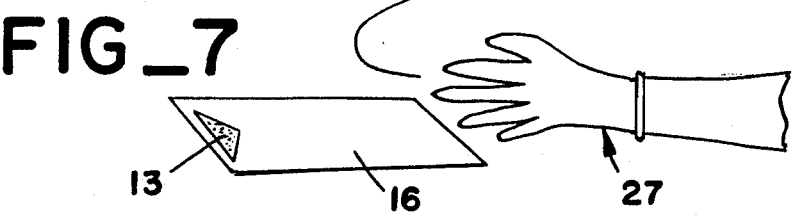
FIG_7
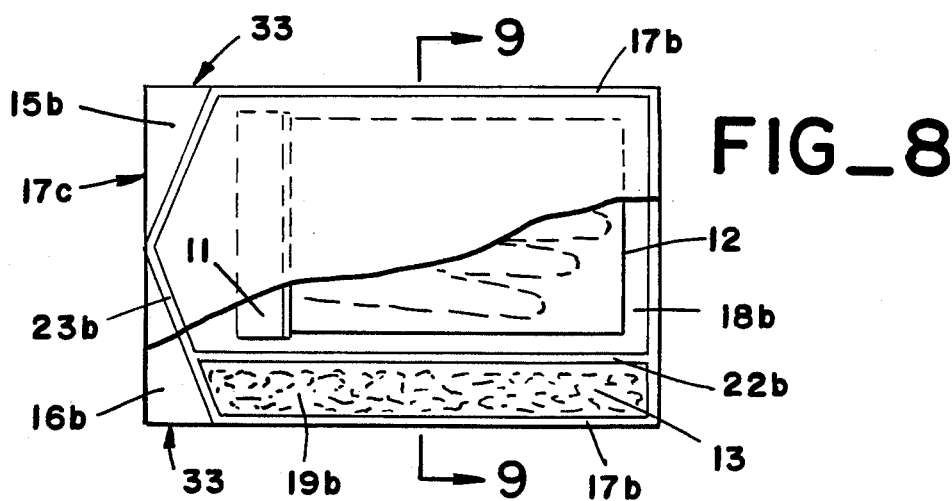
FIG_8
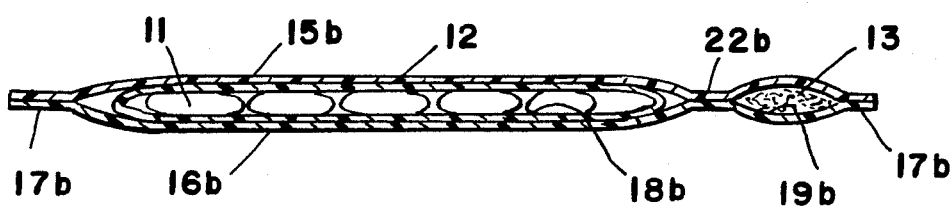
FIG_9

MEDICAL GLOVE AND LUBRICANT DISPENSING PACKAGE

TECHNICAL FIELD

This invention relates to gloves of the type that are lubricated and worn by medical practitioners when it is necessary to insert one or more fingers into openings in a patient's body. More particularly the invention relates to the packaging of such gloves and the lubricant prior to use.

BACKGROUND OF THE INVENTION

Various medical procedures involve the insertion of one or more of a physician's fingers into openings in the patient's body. This is frequently required in the practice of obstetrics, gynecology and proctology among other examples.

The medical practitioner wears a glove during such procedures and in many cases one or more fingers of the glove are lubricated with a gel or the like to facilitate entry into the body opening and to reduce discomfort of the patient. The glove is formed of very thin fluid impervious material, such as latex or the like, to minimize impairment of the practitioner's tactile sensitivity.

The glove must often be sterile in order to prevent introduction of infectious organisms into the patient's body during certain procedures. Such procedures can be undesirably complicated if the sterilizing operation must be performed by medical personnel just prior to use of the glove. Consequently, such gloves are pre-sterilized and sealed into a sterilized package by the manufacturer.

This form of packaging simplifies procedures in that the medical personnel need not take any further steps to sterilize the glove but prior packages of this kind do not address other complications that are encountered in connection with the use of such gloves.

It has been necessary, for example, to have a container of lubricating gel or the like on hand and the container must be opened and reclosed in the process of lubricating the glove. Handling of the gel container can result in contamination of the sterile glove. Inadvertent deposition of the sticky gel on objects other than the glove can also be a problem.

The typically tight and clinging medical glove can also be difficult to put on. The process can be expedited by having another person, such as a nurse, hold the glove open while the physician's hand is being inserted into the glove but this is not always a practical solution. An additional person may not be readily available or an available person may have other pressing activities to perform in connection with the medical procedure.

The present invention is directed to overcoming one or more of the problems discussed above.

SUMMARY OF THE INVENTION

In one aspect, the present invention provides a medical glove and glove lubricant container which includes a package having a first sheet of material that overlays a second sheet of material and which is bonded to the second sheet along zones that define a sealed glove compartment at a first location between the sheets and a separate sealed lubricant compartment at a spaced apart location. The bonding of the sheets along the zones is weaker than the material itself enabling the first sheet to be peeled away to open both of the compartments with a single motion of a person's hands. The medical glove is disposed in the glove compartment and a quantity of the lubricant is disposed in the lubricant compartment.

In another aspect of the invention, the first and second sheets of material have unbonded edges at one end of the package. The zones along which the first and second sheets are bonded together include a first zone situated between the glove compartment and the unbonded edges and a second zone situated between the two compartments. Each of the first and the angle being directed at the unbonded edges.

In another aspect of the invention, a medical glove and lubricant dispensing container includes a package having first and second sealed compartments and is formed in part by a sheet of flexible material that is bonded to the remainder of the package along zones which bound the compartments including a zone which separates the compartments from each other. The bonding is weaker than the material of which the package is formed enabling the sheet to be peeled away from the remainder of the package to thereby open both of the compartments. A glove holder is disposed in the first compartment and has an open end providing access to the interior region of the holder. The finger sheaths and palm enclosing portions of a medical glove are disposed within the interior region of the glove holder while the cuff of the glove extends out of the open end of the holder and is folded back over the outer surface of the holder. The second compartment contains a volume of the lubricant.

In another aspect, the invention provides a packaged medical glove which includes an openable enclosure containing a substantially flat glove holder. The holder has a slit opening at one end that communicates with an interior region of the holder, the holder being formed of material which can be fixed to distend the slit opening into a more rounded configuration. The finger and palm enclosing portions of a medical glove are within the glove holder while the cuff portion extends out of the opening and is folded back against the adjacent region of the outer surface of the holder.

In still another aspect of the invention, the finger enclosing portions of the glove are arranged in the glove holder in a substantially parallel relationship corresponding to the arrangement of the fingers of an opened human hand. The outer surface of the glove has a depiction of the arrangement of the portions of the glove that are within the holder and at least the portion of the enclosure that overlies the depiction is transparent.

The invention simplifies medical procedures that involve insertion of one or more gloved fingers into a body opening by providing the medical practitioner with a single package which contains a glove and a supply of lubricant in separate sealed compartments and which can be easily opened with one simple hand movement. In the preferred form of the invention, the package also contains a flat glove holder which facilitates insertion of the wearer's hand into the glove and which protects the outer surface of the glove from contamination while it is being put on. In particular, the cuff of the glove extends out of the holder through a slit opening at one end of the holder and is folded back against the outer surface of the holder. Compression of opposite edges of the holder with one hand spreads the slit opening and glove cuff into a more rounded shape enabling easy insertion of the other hand. A depiction of the outline of a glove on the outer surface of the holder conforms with the actual orientation of the glove within the holder to further facilitate insertion of the hand.

The invention, including further aspects and advantages thereof, may be further understood by reference to the following description of preferred embodiments and by reference to the accompanying drawings.

BRIEF DESCRIPTION OF THE DRAWINGS

FIG. 1 is a broken out plan view of a medical glove and package in accordance with a first embodiment of the invention.

FIG. 2 is a longitudinal section view of the glove and package of FIG. 1 taken along line 2—2 thereof.

FIG. 3 is a cross section view taken along line 3—3 of FIG. 1.

FIG. 4 is a foreshortened longitudinal section view of a glove and glove holder contained within the package of the preceding figures.

FIG. 5 is a plan view of the package of the preceding figures illustrating opening of the package.

FIG. 6 is an end view of the glove and glove holder as it appears just prior to insertion of a wearer's hand.

FIG. 7 is a diagrammatic view showing actions taken by the wearer after insertion of a hand into the glove.

FIG. 8 is a broken out plan view of a second embodiment of the invention.

FIG. 9 is a section view taken along line 9—9 of FIG. 8.

FIG. 10 is a broken out perspective view of a third embodiment of the invention.

DETAILED DESCRIPTION OF THE PREFERRED EMBODIMENT

Referring initially to FIG. 1 of the drawings, the principal components of this embodiment of the invention are a medical glove 11, a glove holder 12 and a volume of glove lubricant gel 13 all of which are contained within a sealed outer package 14.

Package 14 is formed of flexible, fluid tight material which is preferably of the heat sealable type, polyethylene plastic being a suitable example. The package 14 is rectangular in this example, although other configurations are also satisfactory, and is preferably formed of transparent or semi-transparent material to enable viewing of the contents of the unopened package.

Referring jointly to FIGS. 1 and 2, the package is formed by first and second parallel sheets 15 and 16 of the flexible fluid tight material and the edge regions 17 of the sheets are bonded together around the periphery of the package except along one end 17a which is unbonded to enable insertion of the medical practitioner's fingers during opening of the package as will hereinafter be described in more detail. The bonding at edge regions 17 is preferably accomplished by heat sealing although other techniques, such as application of an adhesive, may also be used. In either case, the bond at edge regions 17 is of less strength than the material of which sheets 15 and 16 are made so that the sheets can be pulled apart when the package 14 is to be opened. This can be provided for by controlling the level of heating during the heat sealing operation or by using an adhesive of appropriate strength.

For most purposes, it is preferable that the package 14 material and the contents of the package such as glove 11 and holder 12 be sterilized by any of the known techniques prior to heat sealing of the edge regions 17 and that the sealing operation be conducted in a sterile environment.

Package 14 has first and second sealed compartments 18 and 19 respectively which are also sealed off from each other. First compartment 18 contains the glove 11 and holder 12 and second compartment 19, which is typically smaller than the first compartment, contains a quantity of glove lubricant 13 which may be of any of the known forms such as a semi-liquid gel.

The second or lubricant containing compartment 19 is located at the back end of package 14 and is separated from the first compartment 18 by a zone 22 along which the opposite walls 15 and 16 of the package are bonded together by heat sealing in this example although adhesives may also be used for the purpose. As in the case of the edge regions 17 of the package, the bonding of the package 14 material along zone 22 is weaker than the material itself so that the sheet 15 may be peeled away from sheet 16 when the package is to be opened.

The bonded zone 22 is preferably angled with the apex of the angle being at the centerline of package 14 and being pointed towards first compartment 18 thereby giving the second compartment 19 a triangular configuration. Zone 22 thus constitutes a so-called chevron seal which can be easily opened by peeling sheet 15 away from sheet 16 as breaking apart of the bond does not occur all at once. Instead, the bond at zone 22 is progressively pulled apart as the stripping away of sheet 15 proceeds.

The sheets 15 and 16 are similarly bonded together along another zone 23 which extends across the package 14 between the glove compartment 18 and the unbonded end edge 17a, the zone 23 being spaced from edge 17a. Zone 23 is also angled in a manner similar to that of zone 22 and thus constitutes a second chevron seal which can be easily opened by peeling sheet 15 away from sheet 16.

Referring jointly to FIGS. 1, 3 and 4, the glove holder 12 is a flat rectangular paper envelope in this example of the invention and is of the type having a slit opening 26 at one end. Folders or pouches formed of material that can be flexed may also be used. The holder 12 is disposed in compartment 18 in an orientation at which the open end 26 is closest to the unbonded end 17a of package 14. The finger sheaths and palm enclosing portions of glove 11 are situated within holder 12 while the cuff 27 of the glove extends out of the holder end opening 26 and is folded back over the adjacent portions of the exterior surface of the holder. Referring to FIG. 1 in particular, the flattened glove 11 is preferably arranged within holder 12 with the thumb and finger sheaths 28 extending in a more or less parallel relationship corresponding generally to the configuration of an opened human hand. It is helpful if the outer surface of holder 12, which is visible through the transparent package 14, is imprinted with an outline of the position of the glove within the holder. The outline is coincident with the glove 11 itself in FIG. 1 and thus both are represented in the drawing by the single dashed line 11. The outline enables the medical practitioner to ascertain if the glove 11 is a right hand glove or a left hand glove before opening the package 14 and serves as a guide for entry of the fingers into the holder 12.

In operation, the package 14 serves passively as a sterile storage container for glove 11 prior to the time that it is to be used. With reference to FIG. 5, the initial step in making use of the glove 11 is to open package 14 by grasping sheets 15 and 16 with separate hands and then peeling sheet 15 away from sheet 16. This opens both the glove compartment 18 and lubricant compartment 19 with the same simple hand movement. Referring to FIG. 6, the glove holder 12 is then grasped by the hand that will not wear the glove and the sides of the holder are compressed with that hand as indicated by arrows 31 in FIG. 6. This flexes the holder 12 in a manner which causes the slit opening 26 and thus the cuff 27 of the glove to gape open and assume a more rounded configuration. This facilitates entry of the other hand into the glove 11.

Referring to FIG. 7, cuff 27 is then rolled back onto the wearer's wrist and holder 12 is withdrawn from the gloved hand and discarded. A notch 32 in the open edge of holder 12 facilitates removal of the holder. The glove 11 may then be adjusted on the hand if complete fitting of the glove has not already occurred. One or more fingers of the glove 11 may then be dipped into the lubricant 13 and, if necessary, sheet 16 may be used as an aid in spreading the lubricant. The medical procedure requiring use of a lubricated glove may then be performed.

The configuration of the glove and lubricant dispensing package can be varied in any of a number of ways, an example of which depicted in FIGS. 8 and 9. The glove compartment 18b and a narrower lubricant compartment 19b of this embodiment extend in side by side relationship. A rectangular sheet 15b of flexible fluid-tight material again overlays a similar sheet 16b of material and the edge regions 17b of the two sheets are bonded together except along a front edge 17c of the package 14b and short adjacent portions 33 of the two side edges of the package. The sheets 15b and 16b are also bonded together along an angled zone 23b having an apex at the center of the unbonded front edge 17c and along a linear zone 22b which isolates compartments 18c and 19c from each other. A glove 11 and holder 12 of the previously described kind is disposed in compartment 18b and compartment 19b contains lubricant 13.

As in the previous embodiment, the bonding of sheets 15b and 16b along edge regions 17b and zones 22b and 23b is of less strength than the material of which the sheets are formed. Thus both compartments can be opened with a single hand motion by grasping the sheets 15b and 16b at one corner of the front edge 17c of the package 14b and stripping sheet 15c away from sheet 16c.

FIG. 10 depicts still another embodiment of the invention in which a sheet 15c of flexible fluid-tight material, which is metal foil in this particular example, overlays a tray-like sheet 16c formed of plastic that is semi-rigid and in which the glove compartment 18c and lubricant compartment 19c are defined by spaced apart dished regions formed in the plastic. This blister type of package 14c can be fabricated in an economical manner by vacuum forming techniques known to the art. Sheets 15c and 16c are again bonded together around the edge regions 17d of the sheets and along a thin linear zone 22c which isolates compartments 18c and 19c from each other with the bonding being of a kind which enables sheet 15c to be peeled away when the package 14c is to be opened. As in the previously described embodiments, compartment 18c contains a glove 11 protected by a glove holder 12 and compartment 19c contains lubricant 13.

While the invention has been described with respect to certain specific embodiments for purposes of example, many modifications and variations are possible and it is not intended to limit the invention except as defined in the following claims.

I claim:

1. A medical glove and glove lubricant container comprising a package having a first sheet of material that overlays a second sheet of material and which is bonded thereto along zones that define a sealed glove compartment at a first location between said sheets of material and a separate sealed lubricant compartment at a spaced apart location between said sheets of material, the bonding of said sheets of material along said zones being weaker than said material enabling said first sheet of material to be peeled away from said second sheet of material to open both of said compartments with a single motion of a persons hands, a medical glove disposed in said glove compartment and a quantity of lubricant disposed in said lubricant compartment.

2. The medical glove and glove lubricant container of claim 1 wherein said glove has finger sheaths and a palm enclosing portion and a cuff portion through which a wearer's hand can be inserted into the glove, further including a glove holder disposed in said glove compartment and having an interior region in which said finger sheaths and palm enclosing portion of said glove are disposed.

3. The medical glove and glove lubricant container of claim 2 wherein said glove holder includes means for opening up said cuff portion of said glove to facilitate entry of a wearer's hand into said glove.

4. The medical glove and glove lubricant container of claim 2 wherein said glove holder has a substantially flat configuration and is formed of flexible material and has an opening at one end providing access to said interior region, said interior region being of sufficient size to receive a human hand through said opening, and wherein said cuff portion of said glove extends out of said opening and is folded back over the region of said glove holder that is adjacent to said opening.

5. The medical glove and glove lubricant container of claim 4 wherein at least said first sheet of material is transparent and wherein said glove is arranged within said glove holder with said finger sheaths in a substantially parallel relationship corresponding to the fingers of an opened human hand, the surface of said glove holder which faces said transparent first sheet of material having an outline thereon which is depictive of the arrangement of the glove within said holder.

6. The medical glove and glove lubricant container of claim 1 wherein at least said first sheet of said material of said package is formed of flexible material.

7. The medical glove and glove lubricant container of claim 1 wherein said zones along which said first and second sheets of material are bonded together include zones extending along the perimeters of said glove compartment and said lubricant compartment including a zone which extends between said glove compartment and said lubricant compartment to isolate said compartments from each other.

8. The medical glove and lubricant container of claim 7 wherein said zone which extends between said glove compartment and said lubricant compartment has an angled configuration.

9. The medical glove and lubricant container of claim 1 wherein said first second sheets of material have unbonded edges at one end of said package and wherein said zones along which said first and second sheets of material are bonded together include a first zone situated between said glove compartment and said unbonded edges and a second zone extending between said glove compartment and said lubricant compartment, each of said first and second zones having an angled configuration with the point of the angle being directed at said unbonded edges.

10. The medical glove and lubricant container of claim 1 wherein said first and second sheets of material have unbonded edges at one end of said package, wherein said glove compartment and said lubricant compartment extend in parallel relationship with each other and at right angles to said unbonded edges, and wherein said zones along which said first and second sheets of material are bonded together include a first zone which extends between said compartments and a second zone which extends across said package between said compartments and said unbonded edges, said second zone being angled with the point of the angle being directed towards said unbonded edges.

11. The medical glove and lubricant container of claim 1 wherein said second sheet of material is formed of material which is rigider than that of said first sheet of material and has a first dished region forming said glove compartment and a second dished region forming said lubricant compartment, and wherein said first sheet of material is relatively flexible and has edge regions bonded to the edge regions of said second sheet of material and is also bonded to said second sheet of material along a zone which extends between said compartments.

12. A medical glove and lubricant dispensing container comprising:
   a package having first and second sealed compartments and being formed in part by a sheet of flexible material that is bonded to the remainder of said package along zones which bound said compartments including along a zone which separates said compartments from each other, said bonding being weaker than the material of said sheet and said remainder of said package enabling said sheet to be peeled away from said remainder of said package to thereby open both of said compartments,
   a glove holder disposed in said first sealed compartment, said glove holder having an interior region and an open end providing access to said interior region,
   a medical glove having finger sheaths and a palm enclosing portion disposed within said interior region of said glove holder and having a cuff portion which extends out of said open end of said glove holder and which is folded back over the outer surface of said glove holder, and
   a volume of lubricant disposed in said second sealed compartment of said package.

13. A medical glove and package therefor comprising an openable enclosure, a substantially flat glove holder disposed in said enclosure and having a slit opening at one end which communicates with the interior region of the holder, said holder being formed of material which can be flexed to distend said slit opening into a more rounded configuration, and a medical glove having finger and palm enclosing portions which are within said interior region of said holder and having a cuff portion which extends out of said opening and which is folded back against the portions of the outer surface of said glove holder that are adjacent said opening.

14. The medical glove and package of claim 13 wherein said finger enclosing portions of said glove are arranged in said glove holder in a substantially parallel relationship corresponding to the arrangement of the fingers of an opened human hand and wherein the outer surface of said glove has a depiction of the arrangement of the portions of the glove that are within said holder, at least the portion of said enclosure that overlies said depiction being transparent.

* * * * *